United States Patent [19]
Davies et al.

[11] Patent Number: 4,693,983
[45] Date of Patent: Sep. 15, 1987

[54] REACTOR FOR CULTIVATING BIOLOGICAL MATERIAL SUCH AS IMMOBILIZED CELLS

[75] Inventors: Graham A. Davies, Macclesfield; Ferda Mavituna, Stockport, both of England

[73] Assignee: National Research Development Corporation, London, England

[21] Appl. No.: 937,063

[22] PCT Filed: Apr. 3, 1986

[86] PCT No.: PCT/GB86/00192
§ 371 Date: Nov. 7, 1986
§ 102(e) Date: Nov. 7, 1986

[87] PCT Pub. No.: WO86/05802
PCT Pub. Date: Oct. 9, 1986

[30] Foreign Application Priority Data
Apr. 4, 1985 [GB] United Kingdom ............. 8508976

[51] Int. Cl.⁴ .................................................. C12M 3/00
[52] U.S. Cl. .................................... 435/284; 435/286; 435/288; 435/311; 435/316
[58] Field of Search ............... 435/284, 286, 288, 300, 435/301, 311, 316, 240, 241

[56] References Cited
U.S. PATENT DOCUMENTS

| | | | |
|---|---|---|---|
| 4,225,671 | 9/1980 | Puchinger et al. | 435/71 |
| 4,230,773 | 10/1980 | Bakos | 428/447 |
| 4,391,912 | 7/1983 | Yoshida et al. | 435/241 |
| 4,514,499 | 4/1985 | Noll | 435/240 |
| 4,603,109 | 7/1986 | Lillo | 435/41 |
| 4,604,361 | 8/1986 | Peters | 435/288 |
| 4,661,458 | 4/1987 | Berry et al. | 435/284 |

FOREIGN PATENT DOCUMENTS

| | | |
|---|---|---|
| 0112155 | 6/1984 | European Pat. Off. . |
| 0113328 | 7/1984 | European Pat. Off. . |
| 0121981 | 10/1984 | European Pat. Off. . |
| 0120285 | 10/1984 | European Pat. Off. . |
| 0155237 | 9/1985 | European Pat. Off. . |
| 839245 | 5/1952 | Fed. Rep. of Germany . |
| 2324365 | 9/1976 | France . |
| 2393849 | 6/1978 | France . |
| WO84/01959 | 5/1984 | PCT Int'l Appl. . |
| WO85/01062 | 3/1985 | PCT Int'l Appl. . |
| 1037759 | 8/1966 | United Kingdom . |
| 1395291 | 5/1975 | United Kingdom . |
| 1448176 | 9/1976 | United Kingdom . |
| 1567899 | 5/1980 | United Kingdom . |
| 2062006A | 5/1981 | United Kingdom . |

OTHER PUBLICATIONS

Lydersen, B. K. et al., "Ceramic Matrix for Large Scale Animal Cell Culture", Biotechnology, Jan. 1985, pp. 63–67.
Jensen, M. D., "Production of Anchorage-Dependent Cell—Problems and Their Possible Solutions", Biotechnology & Bioengineering, vol. XXIII, pp. 2703–2716 (1981).

Primary Examiner—Samuel Scott
Assistant Examiner—Allen J. Flanigan
Attorney, Agent, or Firm—Murray and Whisenhunt

[57] ABSTRACT

A reactor 10 for cultivating biological material is colonized with plant cells 3 in channels 2a of a support matrix. The biological material cannot pass out of the channels. Each colonized channel adjoins several non-colonized channels 2, viz. a nutrient supply channel, an extractant channel, a heat-transfer channel and a gas supply channel. The walls separating the different pairs of these channels are permeable to the relevant material only.

29 Claims, 4 Drawing Figures

REACTOR FOR CULTIVATING BIOLOGICAL MATERIAL SUCH AS IMMOBILIZED CELLS

This invention relates to a reactor for cultivating biological material, such asplant and animal cells immobilised in it.

It has long been recognised that complex chemical reactions taking place in biological systems can be manipulated to form the basis of commercial methods for producing chemicals. Recently attention has been focussed on plant cells and on the possibility of extracting chemical products from such cells.

A variety of different reactor systems are used for biochemical reactions, e.g. stirred and aerated tanks fermenters, trickle bed and percolation "filters" and fluid bed systems. In principle, any of these reactor systems might be suitable for biochemical reactions using plant or animal cells.

There are however some special conditions which must be maintained in many plant cell systems if the cells are to produce material at concentrations which could be considered adequate for a production system. It has been shown that, in order for certain species of plant cells to produce products at exploitable concentrations, the local cell concentration in the reactor must be high or, more particularly, the cells must be in contact with one another as for example in aggregates. These conditions cannot be easily attained in stirred tank reactors unless the cells are supported on a suitable mechanical matrix. Even under these conditions, the cells may be subjected to high shear rates. If mechanical agitation by means of an impeller is used, the aggregates can be broken down. On the other hand, if gas agitation (usually air) is used, the gas bubbles may become trapped in the support matrix, which then floats to the top of tank, whereby the nutrient supply rate to the cells is reduced and cell growth is slowed.

No. EP-A-0121981 (Corning Glass Works) shows a cell culture apparatus which is a high surface area monolithic support comprising a bundle of parallel channels. Anchorage-dependent cells are seeded into the channels, anchor themselves to the walls of the channels, and form a film thereon. Nutrient is supplied along the channels for take-up by the anchored cells. However, as the cells multiplied, they could form agglomerates in the channels which would either block the flow of nutrient or would all be flushed out by the pressure of the nutrient.

An arlucle by Jensen (Biotechnology and Bioengineering, Vol XXIII, pages 2703 et seq.) discloses a cell cultivation method in which a culture vessel is traversed with hollow, capillary tubes through which nutrient or gaseous media flow (much as smoke-flues traverse a steam-raising boiler). The cells grow on the outsides if the tubes in the culture vessel. The walls of the tubes are however selectively permeable, to allow diffusion of the nutrient to the cells and diffusion of gas to and from the gas tubes.

However, this construction has a number of disadvantages. In particular, it is the interfacial area of the cells which is in contact with the nutrient which is important. This area may be low in the Jensen system due to the distance through the cell mass across which the nutrient must travel to reach the most inaccessible cells. Additionally, if the cells became contaminated, the total culture would have to be replaced.

The invention provides a reactor for cultivating biological material colonized therein, conprising a support matrix having a plurality of first channels for being colonized with biological material and defined by bounding walls across which the biological material cannot pass, each said first channel adjoining a second channel and a third channel, the part of said boundary wall adjoining the second channel and the part of said boundary wall adjoining the third channel being of respectively different permeabilities, one such permeability optionally being zero. By 'different permeabilities' is meant being permeable to different materials.

In use of the reactor of the invention, the biological material is localised in the first channels and liquid and/or gas may be transferred between the first channels and the second channels. Thus nutrient is transferred across the porous walls to the biological material contained in the first channels for cultivation thereof. Consequently the nutrient does not actually flow through the first channels, allowing the cells to grow undisturbed. Additionally, the third channels may be used for extraction of products (liquid or gaseous) generated by the biological material, such products diffusing across the porous first-to-third walls. These walls may, as necessary, be coated with a semi-permeable membrane e.g. cellulose acetate. It may however be preferred (in the case of gaseous products) to arrange a gas-permeable tube within the first channel. This would improve product removal by reducing the diffusion path of the gas. Additionally, fourth channels with impervious walls may also be provided within the reactor unit along which a heat-transfer fluid may be supplied to ensure that the biological material is maintained at the optimum temperature. In any case, optionally each said first channel further adjoins a fifth channel, the part of said boundary wall adjoining the fifth channel being permeable to gas but the permeability being different from the other permeabilities. Preferably the second channels, third channels, fourth channels and fifth channels if present are such that no material permeates from any to any other, and preferably do not even adjoin each other.

Thus, according to the invention, a method of cultivating biological material, comprising colonising the first channels of a reactor as set forth above with the biological material, applying nutrient to the second channels, applying extractant fluid to the third channels, applying heat-transfer fluid to the fourth channels if present and applying gas to the fifth channels if present. Furthermore, a biological product may be obtained according to the invention by cultivating biological material in this way and recoving, from the circulated extractant fluid, the product which had become extracted into it.

The reactor may be used for cultivating any type of biological material but is particularly suitable for cultivating animal or plant cells. The unit is most suitable for anchorage-dependent plant cells such as carrot or pepper (example of umbelliferous and solanaceous species) as it allows such cells to grow in contact with each other (i.e. in aggregates) without being "flushed away" by nutrient flow. Plant cells tend to perform best in somewhat large aggregates, and thus channels of at least some 50 mm$^2$ cross-sectional area are preferred, e.g. 64 mm$^2$ or more.

The biological material may be introduced into the reactor by any suitable means. Generally however the first channels (which are intended to receive the biological material) will have at least one open end through which the material may be introduced. The channels may subsequently be closed if desired by any suitable means.

Preferred features and constructions of the reactor and the method by which it is used for cultivating biological material are given below.

Preferably, in the case of anchorage-dependent cells, the channels of the reactor which contain the biological material are not only porous as necessary for nutrient permeation etc. but are "rough" on the micro-scale to enhance adhesion between the biological material and the walls of the channel (or compartment).

The cross-sectional size of the compartments containing biological material depends on the size of the aggregates to be accommodated but will generally be at least 5-10 mm across if square, e.g. 7 mm or 8 mm to 10 mm.

The support matrix of the reactor may comprise a plurality of tubes supported together in axially parallel adjacent relationship. Certain ones of the tubes will form the first channels for the biological material and others will provide the other channels for the supply of nutrient etc. The wall materials and/or wall thicknesses of the tubes will be selected to allow for the transfer of nutrient across the tube walls, other tube walls being selectively permeable to only some other relevant material.

Alternatively the support matrix of the reactor may be a monolith structure formed by extrusion. The monolith will for preference be of a honeycomb-type structure with open-ended cells in the form of tubes or channels extending parallel to each other between opposed walls of the structure.

The cells of the monolith structure will preferably be of constant cross-section along their length and may, for example, be of circular, square, rectangular or triangular, or hexagonal cross-section.

The monolith strucrure may be of a plastics material but for preference is of a material of higher surface energy, e.g. a ceramic material or a metal-metal oxide material. A preferred ceramic material comprises an alumina/silica (carburite/mullite) mixture. Extruded monolith blocks of such material incorporating cells extending between opposite faces which, though not in all respects ideal, are suitable after further modification to be converted into reactors are described in EP-A-No. 0121981.

In order to produce a reactor from the ceramic monoliths described above it is envisagedthat the ceramic material will firstly be leached in an acid or alkali to render all interior walls porous. If it is envisaged that certain of the cells will ultimately be used for the supply of heat-transfer fluid (so that they must have non-porous walls) then further treatment of monolith will be required. This treatment will entail treating those walls (i.e. the walls of the fourth channels) which are to become non-porous with a glaze and firing the monolith to fuse the glaze. Any of the porous cells which are ultimately to be used as third channels for the extraction of products generated by the biological material may be treated with a semi-permeable membrane (e.g cellulose acetate). The fifth (gas supply) channels (if present) may have diluted glaze applied, and the glaze mildly leached, to form gas pores.

The reactor may be used in a variety of ways. For example, the reactor (colonised with biological material in certain channels thereof) may be immersed in a suitable vessel (e.g. an agitated tank reactor) in nutrient which is caused to pass through at least some of the first channels for transfer across the walls thereof to the biological material. Such a method does however suffer from the disadvantage that the whole reactor must be immersed in the nutrient, with problems arising from large liquid hold-up and sterilisation difficulties.

Alternatively, in accordance with a more preferred aspect of the invention, at least some of the second channels are associated with inlet conduit means for the supply to these second channels of nutrient and also with outlet conduit means for the removal of nutrient from the channels. The inlet and outlet conduit means may be multiplexed together whereby nutrient media flows successively through a plurality of the first channels, or a parallel-flow arrangement may be adopted. Additionally, certain of the third channels may be used for removal of products generated by the biological material and for this purpose each of these channels will be associated with respective inlet and outlet conduits (preferably multiplexed) for a suitable extractant fluid. Similarly, any fourth channels used for heat-transfer fluid will have their own respective inlet and outlet conduits for heat-transfer media (again preferably multiplexed).

With this embodiment of the invention, the need to immerse the reactor in a nutrient liquid is avoided.

Having regard to the foregoing description, it should be noted that the present invention has a number of significant advantages as set out below:

1. Since the nutrient is not supplied along those channels which are colonised with biological material, it is possible to use high nutrient velocities without displacing the biological material, thereby allowing relatively constant nutrient concentration along the length of the reactor.

2. The system will give a higher packing efficiency for cellular material and better contact with transfer surfaces. In the case of extruded monoliths using square or triangular channels these shapes both represent tesselations giving optimum packing efficiency. Thus more cell material can be accommodated per unit section of reactor. If a monolith core is constructed of flexible tubes, these again can be arranged to form near space filling shapes to achieve high packing efficiency. The system can be arranged so that the channels can have three, four or six adjacent channels forming space filling shapes according to triangular, square or hexagonal sections. This gives some flexibility in design for varying the area between cells and utility channels (nutrient, extractant and heat control) whilst maintaining maximum packing fraction.

3. Because the cells are localised in predetermined compartments the core could be innoculated with different types of cells. Thus consecutive biochemical reactions could be carried out in the same reactor, such as systems where enzymes excreted from one type of cell are required to actuate other cellular reactions.

4. Because the cells are confined to predetermined compartments the possibility of contamination is minimised. If any channels are contaminated this need not result in a complete loss of culture, but the contaminated compartment(s) could be isolated and flushed without disturbing the rest of the core.

5. It should be easier to sterilised the compact core structure proposed and to minimise the risk of contamination. The overall reaction volume per unit mass of cells is lower. This together with the feature of separated compartments assits in maintaining sterile conditions.

6. The capacity of the reactor, based on product per unit volume of reactor, should be higher in the case of the monolith structure for reasons associated with (2), (4), (5).

The invention will be further described by way of example only with reference to the accompanying drawings, in which.

Figure 1:
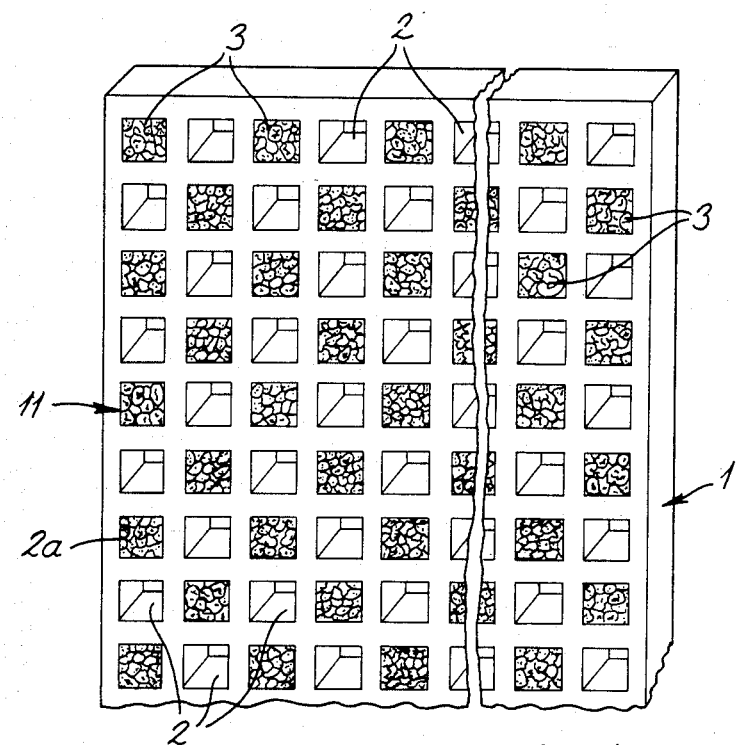
FIG. 1 shows a support matrix colonised with plant cell material.

As illustrated in FIG. 1, an extruded ceramic support matrix 1 comprises a grid formed with rows of open-ended square section compartments of channels 2 some of which (11) are shown as being colonised with aggregates of plant cells 3. As shown in FIG. 1, only alternate compartments 2 of any one row are colonised, and the colonised cells of adjacent rows are in staggered relationship. The walls defining the channels 2a are such that the cells 3 cannot pass across the walls whereby each aggregate of cells 3 is localised in one particular channel 2a. However, the walls between the colonised compartments 2a and the non-colonised channels 2 are porous to allow transfer of nutrient to the compartment 2a. The cells 2 are introduced into the selected channels 2 by innoculation (e.g. by pumping). The cells may then be grown in the matrix 1 and the ends of the compartments 2a may be sealed to produced a reactor in accordane with the invention.

Figure 2:
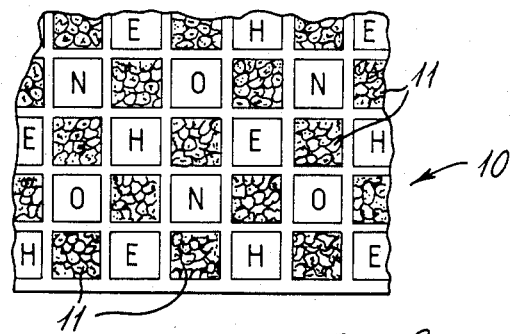
FIGS. 2 and 3 are each a front view of an embodiment of a reactor in accordance with the invention (but omitting details of supply conduits)
Figure 3:
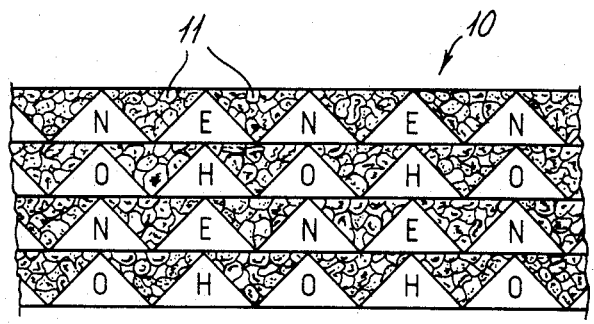

Examples of the use of the reactor are shown in FIGS. 2 and 3.

As shown in FIG. 2, a support matrix 10 (which may be similar to the support matrix 1 shown in FIG. 1) includes selectively colonised channels 11 alternating with non-colonised channels in chess-board manner. The colonised channels 11 may be optionally closed at one or both ends to confine the cells therein. The non-colonised channels in the matrix 11 include nutrient channels N, oxygen channels O, heat-exchange channels H for heating or cooling and extraction channels E; these are arranged with one pair of types alternating in one row and the remaining pair of types alternating in the next row, consecutive rows of a given pair-type themselves being staggered. Each colonised channel 11 thus adjoins (on respective walls) each type of non-colonised channel N, O, H and E, and the walls of each type of non-colonised channel adjoin only colonised channels. These said respective walls have permeabilities appropriate to their function. Thus the wall 11/N allows nutrient to permeate from the channel N into the colonised channel 11. The wall 11/O has smaller pores, allowing gas to permeate from the channel O into the colonised channel 11 but not allowing liquid from the colonised channel to exude into the channel O. Alternatively to smaller pores, the pores can have a hydrophobic coating. The wall 11/H is non-porous, i.e. impermeable, so that only heat, and no mass, is transferred across that wall. This may be achieved by glazing that wall, by passing glazing material through all the channels H. Finally the wall 11/E is adapted to transfer metabolic product from the channel 11 into the extraction channel E. These transfers can be assisted by judicious use of solvent extractants in various phases, or by varying osmotic pressure, physical pressure and, for the walls 11/O where hyperoxygenation might be a difficulty, gaseous partial pressures.

Semi-permeable membranes with appropriate properties may also be used, or the relevant walls may be coated with agents having appropriate functional groups to attract or repel substances from permeating the walls as appropriate. Such an arrangement is shown in FIG. 3, where a reactor is shown, which has been constructed according to corrugation-reinforced cardboard sheet technology, using instead semi-permeable membranes.

The channels are of triangular cross-section arranged in rows of one triangle height. Alternate triangles (those pointing "downwards" in the Figure) are colonised channels 11. The channels N, O, H and E are arranged with one pair of types alternating in one row and the remaining pair of types alternating in the next row. Each colonised channel thus adjoins one of each type of non-colonised channel, and each non-colonised channel adjoins only colonised channels 11.

The channels N may be multiplexed together for the supply thereto, and removal therefrom, of nutrient. Similarly, the extraction channels R may be multiplexed together, as may be the heat-transfer channels H. The multiplexing can follow one of two principles for each one of N, O, H and E. In the first possibility, nutrient (for example) is introduced into one end of a channel N; it leaves by the other end, where a small U-shaped duct returns the partly used nutrient into one end of a second channel N. On leaving the other end of the second channel, it may be ducted into a third channel, and so on, until it has traversed all the channels N in series.

In the second possibility, oxygen (for example) is fed into a manifold which divides the stream of oxygen into a multiplicity of small streams, each ducted into a respective channel O, in parallel. Combinations, such as series-parallel and parallel-series ducting, are possible, and the arrangement can differ, if thought appropriate, between the nutrient, oxygen, heat-transfer fluid and extractant ductings. As a further refinement, the various fluids may flow co-current to countercurrent as thought best. Similarly, the extraction channels E have multiplexed inlet and outlet conduits as similar multiplexed condutis are provided for the heat-transfer channels H.

Figure 4:
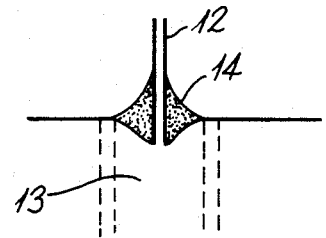
FIG. 4 illustrates a capillary connection to a channel of the support matrix shown in FIG. 2.

A suitable connection for supplying (or removing) fluid to any one of channels N, O, H, or E is shown in FIG. 4. A capillary connection 12 is fixed to the channel 13 by resin or silicone rubber 14.

It will therefore been seen that the reactor illustrated in FIGS. 1 to 3 is provided with all services required for the growth of cells and extraction of products therefrom. Since the nutrient channels N, gas channels O, heat flow channels H and extraction channels E are each provided with the necessary fluids through multiplexed capillary connections there is no need to immerse the support matrix in a liquid. The nutrient may be an aqueous glucose solution. The plant cells may be carrot or capsaicin. The extractant may be oil. The heat-transfer fluid may be anything since it passes through imperviously-walled channels only. The gas may be air.

We claim:

1. A reactor for cultivating biological material colonized therein, comprising a support matrix having a plurality of first channels for being colonized with biological material and defined by bounding walls across which the biological material cannot pass, each said first channel adjoining a second channel and a third channel and a fourth channel, the part of said boundary wall adjoining the second channel and the part of said boundary wall adjoining the fourth channel being respectively permeable to different materials.

2. A reactor according to claim 1, the part of said boundary wall adjoining the fourth channel being permeable to no materials.

3. A reactor according to claim 1, wherein each said first channel further adjoins a fifth channel, the part of said boundary wall adjoining the fifth channel being permeable to gas but the permeability being different from the other permeabilities.

4. A reactor according to claim 1, wherein the second channels, third channels, fourth channels and fifth channels if present are such that no material permeates from any one to any other.

5. A reactor according to claim 4, wherein the second channels, third channels, fourth channels and fifth channels if present are so arranged as not to adjoin each other.

6. A reactor according to claim 1, wherein the different permeabilities are provided by different pore sizes.

7. A reactor according to claim 1, wherein the different permeabilities are provided by selective surface treatment of respective parts of said boundary wall.

8. A reactor according to claim 1, wherein the support matrix is a monolithic structure comprising a plurality of parallel channels extending between opposed faces of the structure.

9. A reactor according to claim 8, wherein the channels of the monolith are of constant cross-section along their length.

10. A reactor according to claim 8, wherein the support matrix is of a ceramic material.

11. A reactor according to claim 1, wherein the second channels are connected to inlet conduit means and outlet conduit means for supplying and removing nutrient, the first/second channel boundary walls being permeable to nutrient.

12. A reactor according to claim 11, wherein said inlet and outlet conduit means are arranged to supply nutrient successively through a plurality of the second channels.

13. A reactor according to claim 11, wherein said inlet and outlet conduit means are arranged to supply nutrient in parallel through the second channels.

14. A reactor according to claim 1, wherein the third channels are extraction channels for the removal of desired products generated by the biological material, the first/second channel boundary walls being permeable to said desired products unlike the first/second channel boundary walls.

15. A reactor according to claim 14, wherein said third channels are provided with a semi-permeable membrane.

16. A reactor according to claim 1, wherein the third channels are permeable walled tubes within said first channels.

17. A reactor according to claim 14, wherein the third channels are connected to inlet conduit means and outlet conduit means for supplying and removing extractant fluid.

18. A reactor according to claim 17, wherein the inlet and outlet conduit means for the extractant fluid are arranged to supply extractant fluid successively through a plurality of the third channels.

19. A reactor according to claim 17, wherein the inlet and outlet conduit means for the extractant fluid are arranged to supply extractant fluid in parallel through the third channels.

20. A reactor according to claim 1, wherein all the channels are of substantially similar cross-sectional area.

21. A reactor according to claim 1, wherein the channels are of at least 50 $mm^2$ cross-sectional area.

22. A reactor according to claim 21, wherein the channels are of at least 64 $mm^2$ cross-sectional area.

23. A method of cultivating biological material, comprising colonizing the first channels of a reactor according to claim 1 with the biological material, applying nutrient to the second channels, applying extractant fluid to the third channels, applying one of a heat-transfer fluid of a gas to the fourth channels and applying the other of a heat-transfer fluid or a gas to the fifth channels if present.

24. A method according to claim 23, wherein the biological material is anchorage-dependent cells.

25. A method according to claim 24, wherein the biological material is plant cells.

26. A method according to claim 25, wherein the plant cells are of solaneceous or umbelliferous species.

27. A method according to claim 23, wherein the extractant fluid is an oil.

28. A method according to claim 23, wherein the nutrient is an aqueous sugar solution.

29. A method of obtaining a biological product, comprising cultivating biological material by a method according to claim 23, and recovering from the circulated extractant fluid the product which had become extracted into it.

* * * * *